(12) United States Patent
Kim et al.

(10) Patent No.: US 7,452,669 B2
(45) Date of Patent: Nov. 18, 2008

(54) MICRO PCR DEVICE, METHOD OF AMPLIFYING NUCLEIC ACID AND METHOD OF MEASURING CONCENTRATION OF PCR PRODUCT USING THE SAME

(75) Inventors: Sang-hyo Kim, Yongin-si (KR); Jung-im Han, Seoul (KR); Chin-sung Park, Yongin-si (KR); Jin-tae Kim, Hwaseong-si (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 10/931,522

(22) Filed: Sep. 1, 2004

(65) Prior Publication Data

US 2005/0095624 A1    May 5, 2005

(30) Foreign Application Priority Data

Oct. 30, 2003   (KR) ................. 10-2003-0076216

(51) Int. Cl.
*C12Q 1/68*   (2006.01)
(52) U.S. Cl. .............. 435/6; 435/283.1; 435/285.2; 435/287.2
(58) Field of Classification Search ............... 435/6, 435/91.2, 287.2
See application file for complete search history.

(56) References Cited

U.S. PATENT DOCUMENTS

| 4,927,752 | A | * | 5/1990 | Remacle | ............... 435/7.92 |
|---|---|---|---|---|---|
| 5,935,793 | A | * | 8/1999 | Wong | ............... 435/6 |
| 6,168,948 | B1 | * | 1/2001 | Anderson et al. | ......... 435/287.2 |
| 6,169,394 | B1 | * | 1/2001 | Frazier et al. | ............. 324/71.4 |
| 6,689,478 | B2 | * | 2/2004 | Laguitton | ............... 428/441 |
| 2002/0072054 | A1 | * | 6/2002 | Miles et al. | ............... 435/6 |
| 2004/0121339 | A1 | * | 6/2004 | Zhou et al. | ............... 435/6 |

FOREIGN PATENT DOCUMENTS

| WO | WO 0159154 A2 | * | 8/2001 |
|---|---|---|---|
| WO | WO 0229027 A1 | * | 4/2002 |

OTHER PUBLICATIONS

"Microchip-based capillary electrophoresis of human serum proteins"; Authors: Christa L. Colyer, Shakuntala D. Mangru, D. Jed Harrison; Journal of Chromatography A, vol. 781, Issues 1-2, Sep. 26, 1997, pp. 271-276.

"Design of an electronic interface for capacitively coupled four-electrode conductivity detection in capillary electrophoresis microchip"; Authors: F. Laugere, G.W. Lubking, J. Bastemeijer, M.J. Vellekoop; Sensors and Actuatiors B: Chemical, vol. 83, Issues 1-3, Mar. 15, 2002, pp. 104-108.

"Contactless Conductivity Detector for Microchip Capillary Electrophoresis"; Pumera et al., Anal. Chem., 2002, 74(9), pp. 1968-1971; Authors: Martin Pumera, Joseph Wang, Franktisek Opekar, Ivan Jelinek, Jason Feldman, Holger Lowe and Steffen Hardt.

* cited by examiner

*Primary Examiner*—Gary Benzion
*Assistant Examiner*—Christopher M. Babic
(74) *Attorney, Agent, or Firm*—Cantor Colburn LLP

(57) ABSTRACT

A micro PCR device comprising an amplification chamber is provided. The amplification chamber has an inner surface coated with a polycationic polymer or a polyanionic polymer and includes electrodes.

12 Claims, 3 Drawing Sheets

United States Patent US 7,452,669 B2

MICRO PCR DEVICE, METHOD OF AMPLIFYING NUCLEIC ACID AND METHOD OF MEASURING CONCENTRATION OF PCR PRODUCT USING THE SAME

BACKGROUND OF THE INVENTION

This application claims the benefit of Korean Patent Application No. 2003-76216, filed on Oct. 30, 2003, in the Korean Intellectual Property Office, the disclosure of which is incorporated herein in its entirety by reference.

1. Field of the Invention

The present invention relates to a micro PCR device, a method of amplifying a nucleic acid using the same, and a method of measuring the concentration of a PCR product by measuring an electrical signal.

2. Description of the Related Art

Conventional PCR showing only qualitative result of amplified DNA via an electrophoresis at the end point of the reaction had many problems in terms of accuracy in the quantitative detection of DNA and the like. To resolve these problems, a real-time PCR device capable of quantitatively analyzing DNA by detecting the intensity of fluorescence proportional to the concentration of amplified DNA via an optical detecting system was developed.

Quantitative analysis of DNA is essential to the treatment of diseases and the study of DNA expression. For example, in the case of a hepatitis patient infected with the hepatitis B virus (HBV), the tolerance of the virus to an administrated drug must be regularly examined by quantitatively measuring the concentration of HBV in the patient's blood plasma via real-time RT-PCR for successful drug treatment.

Conventional real-time PCR required various optical devices such as a filter in addition to a laser source, a micromirror, and a microscope and used expensive fluorescent dyes. Many PCR chips for DNA quantitative analysis were also developed. However, conventional real-time PCR chips were based on a fluorescence detection principle, and thus had many drawbacks in terms of miniaturization and cost.

To resolve these problems, efforts to electrically detect DNA using capillary electrophoresis were made [Christa L. Colyer et al., Journal of Chromatography A, Volume 781, Issues 1-2, 26 Sep. 1997, pp. 271-276; F. Laugere et al., Sensors and Actuators B: Chemical, Volume 83, Issues 1-3, 15 Mar. 2002, pp. 104-108; Pumera et al., Anal. Chem., 2002, 74(9), pp. 1968-1971]. The electrical detection of DNA makes qualitative analysis possible but has many problems in terms of quantitative analysis. Since it is troublesome to transfer a PCR product to a capillary electrophoresis detection system via a microchannel after completing the PCR and since a high voltage is required, it costs much and miniaturization of the detection apparatus is difficult to achieve.

Milles et al. filed a patent application based on a concept that as the concentration of DNA increases during a PCR, resistance decreases and conductivity increases [U.S. Patent Publication No. 2002/0072054 A1]. It is noted that a PCR chip used in the present application is an end-point detection PCR chip rather than the real-time PCR chip. Further, an ionically-labeled probe must be used to detect a PCR product.

Meanwhile, a reproducible signal could not be detected by the conventional detection methods using an electrical or chemical signal. This is believed to be because components in a PCR mixture, such as protein, ion, and stabilizer, adsorb to an electrode surface or an inner surface of an amplification chamber. Such adsorption is very thermodynamically instable and is also affected by fluid mechanical factors. Thus, it is known that the degree of adsorption is changed, even by surrounding minor stimuli such as temperature and electromagnetic force.

The inventors found a method capable of reproducibly measuring a PCR product using an electrical signal, even at a high temperature (a maximum temperature of about 100° C.), by coating a polycationic polymer or a polyanionic polymer on the inner surface of an amplification chamber while carrying out an intensive study to resolve the problems in conventional techniques, and thus completed the present invention.

SUMMARY OF THE INVENTION

The present invention provides a micro PCR device capable of reproducibly amplifying a PCR product using an electrical signal.

The present invention also provides a method of amplifying a nucleic acid using the micro PCR device.

The present invention also provides a method of measuring the concentration of a PCR product using the micro PCR device.

According to an aspect of the present invention, there is provided a micro PCR device comprising an amplification chamber, the amplification chamber having an inner surface coated with a polycationic polymer or a polyanionic polymer and including electrodes.

According to another aspect of the present invention, there is provided a method of amplifying a nucleic acid, the method comprising:

adding a PCR mixture to an amplification chamber in the micro PCR device of the present invention so as to allow the PCR mixture to adsorb to the amplification chamber; and performing a PCR.

According to another aspect of the present invention, there is provided a method of detecting a PCR product, the method comprising:

adding a PCR mixture to an amplification chamber in the micro PCR device of the present invention so as to allow the PCR mixture to adsorb to the amplification chamber;

performing a PCR;

generating an electric field between electrodes; and measuring an electrical signal of the PCR mixture.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
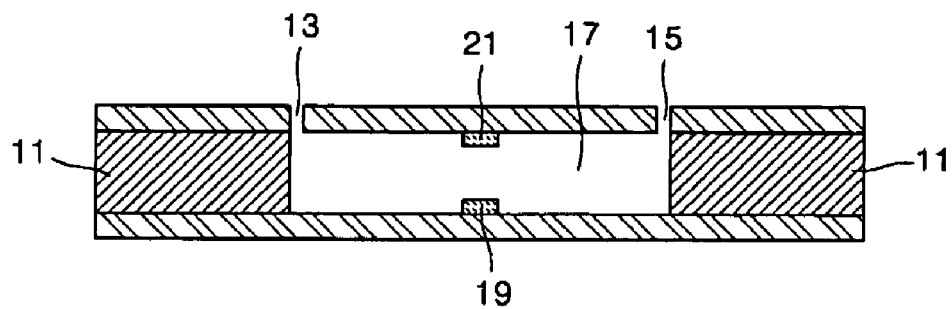
FIG. 1 is a schematic diagram of a micro PCR chip used in the Examples of the present invention.

According to an embodiment of the present invention, there is a micro PCR device including an amplification chamber. The amplification chamber has an inner surface coated with a polycationic or polyanionic polymer and includes electrodes.

Examples of the polycationic polymer include, but are not limited to, polylysine, poly(diallyl dimethyl ammonium chloride) (PDADMAC) (formula I), poly(allylamine hydrochloride) (PAH) (formula II), and poly(ethylene imine) (PEI) (formula III). Examples of the polyanionic polymer include, but are not limited to, poly(sodium styrenesulfonate) (PSS) (formula IV) and the like. These polycationic polymers or polyanionic polymers are coated on the inner surface of the amplification chamber so as to allow a specific component in a PCR mixture to evenly and rapidly adsorb to the coated inner surface. As a result, when an electrically generated signal is detected so as to detect or quantitatively analyse a PCR product, the result is reproducible.

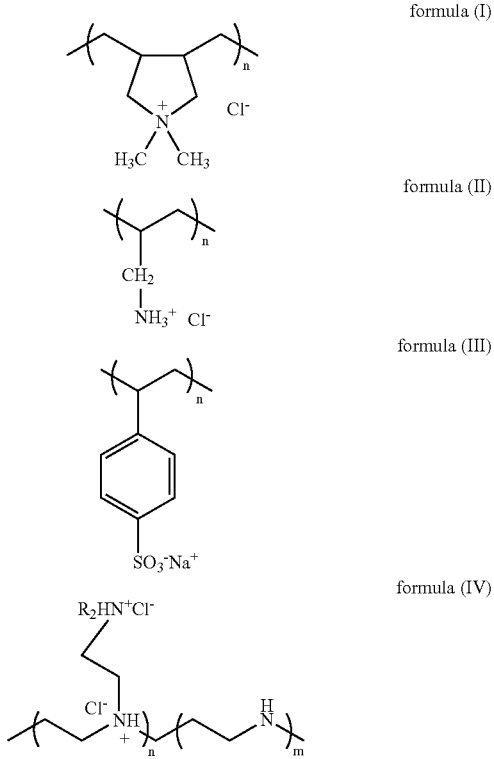

The polycationic polymer or polyanionic polymer may be coated alternately in an arbitrary order on the inner surface of the amplification chamber. For example, the polycationic polymer may be first coated on the inner surface of the amplification chamber and then the polyanionic polymer may be coated thereon, thereby obtaining an amplification chamber having an inner surface composed of the polyanionic polymer, or the polycationic polymer is further coated on the polyanionic polymer layer, thereby obtaining the amplification chamber having the inner surface composed of the polycationic polymer. Conversely, the polyanionic polymer is first coated on the inner surface of the amplification chamber, and then the polycationic polymer is coated thereon, thereby obtaining the amplification chamber having the inner surface composed of the polycationic polymer, or the polyanionic polymer is further coated on the polycationic polymer layer, thereby obtaining the amplification chamber having the inner surface composed of the polyanionic polymer. The number of coatings of the polycationic polymer and the polyanionic polymer is not particularly restricted. The coating process is performed 20 times or less and may be performed 10 times or less.

The micro PCR device according to an embodiment of the present invention may further include an impedance analyzer. The micro PCR device may include elements typically required in a PCR device such as, for example, a heater, a cooler, and a temperature controller. A lab-on-a-chip may further include devices required for preparing a sample and measuring a PCR product. Such conventional micro PCR devices are well known to those skilled in the art.

The amplification chamber may be composed of any material capable of enduring thermal cycling during the PCR, such as quartz, glass, and silicone. Such material is well known in the art.

According to another embodiment of the present invention, there is provided a method of amplifying a nucleic acid, the method including: adding a PCR mixture to an amplification chamber in a micro PCR device according to an embodiment of the present invention so as to allow the PCR mixture to adsorb to the amplification chamber; and performing a PCR. The "PCR mixture" is a reaction mixture for performing a thermal cycling reaction for the amplification of a nucleic acid. The reaction mixture includes, for example, dNTP, ions such as $Mg^{2+}$, nucleic acids such as a primer, and proteins such as polymerase.

According to another embodiment of the present invention, there is also provided a method of detecting a PCR product, the method including: adding a PCR mixture to an amplification chamber in a micro PCR device according to an embodiment of the present invention so as to allow the PCR mixture to adsorb to the amplification chamber; performing a PCR; generating an electric field between electrodes; and measuring the electrical signal of the PCR mixture.

In the method, the PCR mixture is added to the amplification chamber so as to allow components of the PCR mixture to rapidly and evenly adsorb to the amplification chamber having a coating of a polycationic or polyanionic polymer.

In the method, the "PCR" is a polymerase chain reaction amplifying a nucleic acid by repeating denaturation, annealing, and extension and is well known to those skilled in the art. The temperature and time of each process may be appropriately controlled considering the used polymerase, target nucleic acid sequence to be amplified, used primer sequence, and the like.

In the method, an electric field is induced between electrodes so as to generate an electrical signal. Since the generated electrical signal is reproducibly changed depending on the concentration of the amplified nucleic acid, the PCR product can be measured by measuring the electrical signal. The PCR mixture rapidly and evenly adsorbs to the amplification chamber due to the coating of the polycationic polymer or polyanionic polymer, thereby obtaining high reproducibility. When the coating of the polycationic or polyanionic polymer is absent, the obtained electrical signal seriously fluctuates, and thus low reproducibility is obtained.

In the method, the electric field may be generated using an alternating current with a frequency range of 1 Hz-100 MHz. Also, the electric field may be generated using an alternating current voltage with an average voltage (Vrms) of 1 mV-10 V. However, the voltage is not restricted to the above range, and any form of voltage may be applied.

In the method, the electrical signal of the PCR mixture is measured so as to determine the concentration of the PCR product. Examples of the electrical signal include dielectric loss, dielectric constant, and admittance.

The present invention will be described in greater detail with reference to the following examples. The following examples are for illustrative purposes and are not intended to limit the scope of the invention.

EXAMPLES

Example 1: Coating of a Polycationic Polymer

The inner surface of an amplification chamber (material: glass, capacity 1 µl) included in a micro PCR chip was coated by adding 3 g/mL of PDADMAC in 0.5M NaCl to the amplification chamber and leaving it for 20 minutes. Then, the coated inner surface was washed with distilled water and left for 30 minutes or more so as to allow the inner surface to dry.

The formation of a coating layer was identified by measuring the contact angle of the inner surface of the amplification chamber coated with the polycationic polymer, using a contact angle meter (FACE, Japan). The obtained results are shown in Table 1.

TABLE 1

Contact angle of the amplification chamber coated with the polycationic polymer layer (unit: degrees)

| Surface to be coated | Before coating | After coating |
| --- | --- | --- |
| Glass (SiO$_2$) surface | 45 ± 0.5 | 19 ± 0.5 |
| Platinum electrode | 91 ± 0.5 | 70 ± 0.5 |

Referring to Table 1, the contact angle measured before coating remarkably decreased compared to the contact angle measured after coating, indicating that the coating layer of the polycationic polymer was formed on the inner surface of the amplification chamber. In other words, the contact angle of the glass surface decreased due to a hydrophilic polymer coating, which could support that the coating layer was formed.

Example 2: Measurement of an Electrical Signal of Real-Time PCR

A PCR was performed using the micro PCR chip including the micro PCR device having the amplification chamber, of which the coating layer of the polycationic polymer was formed on the inner surface as described in Example 1, and an electrical signal, i.e., impedance, was measured, so that the concentration of the PCR product can be determined in real time. The micro PCR chip (Samsung, Korea) used included an amplification chamber provided with platinum electrodes. The amplification chamber was composed of glass and had a capacity of about 1 µl. A schematic diagram of the used micro PCR chip is illustrated in FIG. 1. FIG. 1 is a side cross-sectional view of the micro PCR chip and illustrates an inlet 13, an outlet 15, a lower electrode 19 and a upper electrode 21, an amplification chamber 17, and a glass wafer 11.

First, a PCR mixture (200 nM of each of dNTP, DNA polymerase (0.1 U/µl), and primers (SEQ ID Nos. 1 and 2)) was added to the amplification chamber 17. Then, 0.1 µg of a template DNA was added to the amplification chamber 17, and a PCR was performed. The PCR conditions include denaturation at 94° C. and for 30 seconds, annealing at 60° C. and for 30 seconds, extension at 72° C. and for 1 minute 30 seconds, and the PCR was executed for 30 cycles.

Figure 2:
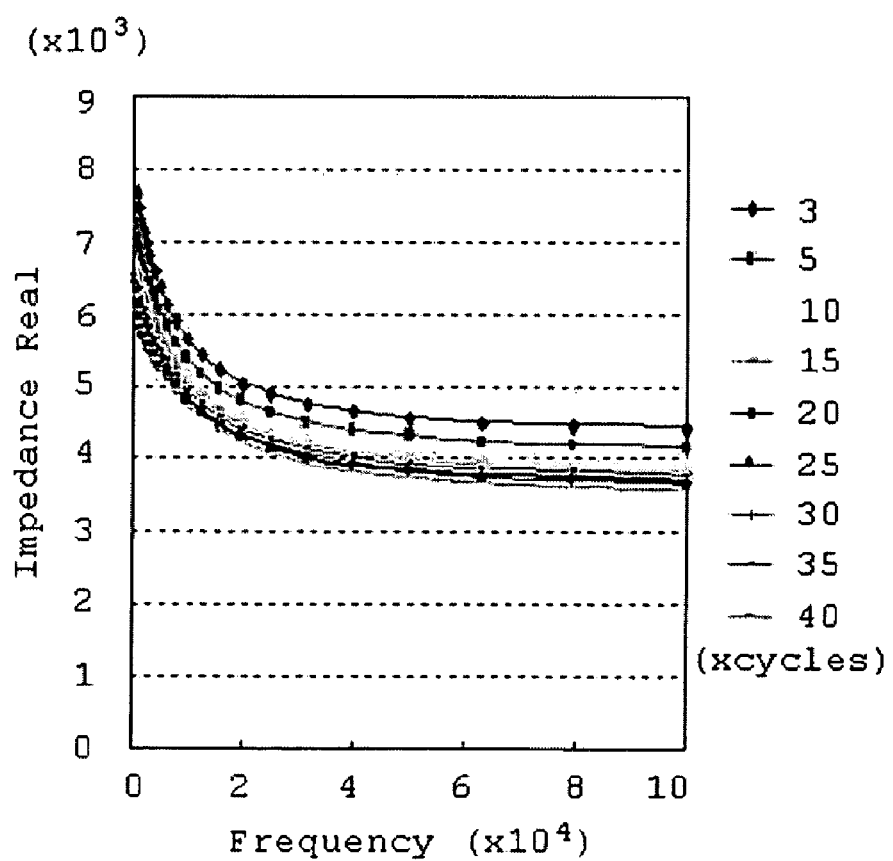
FIG. 2 is a Bode plot illustrating results measured for a 1,000-100,000 Hz sweep, at 10 mV of an alternating current voltage, and $10^6$ copies of HBV DNA during 40 cycles.
Figure 3:
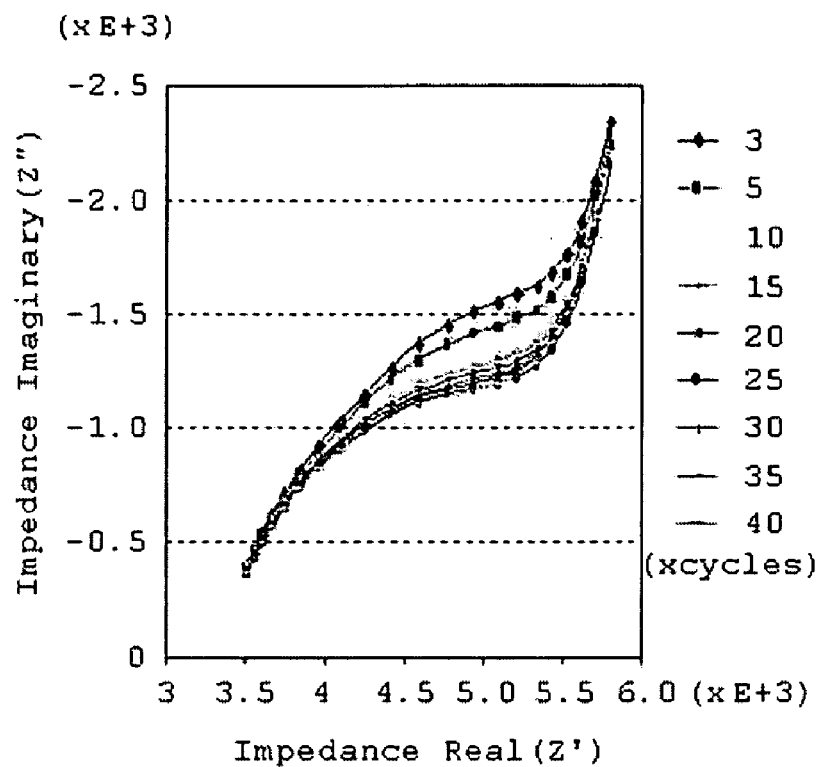
FIG. 3 is a Nyquist plot of the results of FIG. 2.
Figure 4:
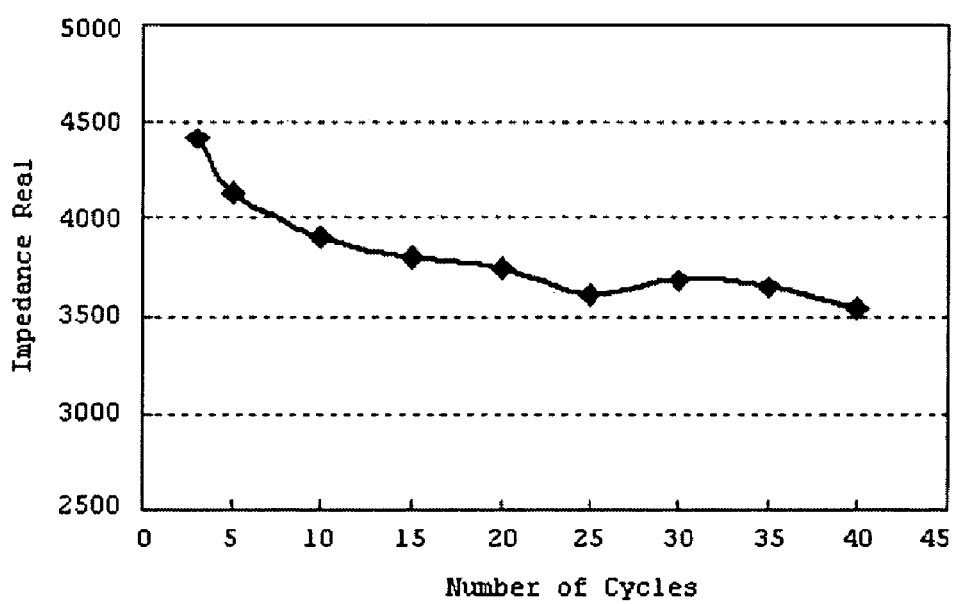
FIG. 4 illustrates the impedance values of an amplified product measured at 100,000 Hz with 10 mV of alternating current voltage and $10^6$ copies of HBV DNA during 40 cycles, with respect to the number of PCR cycles.
Figure 5:
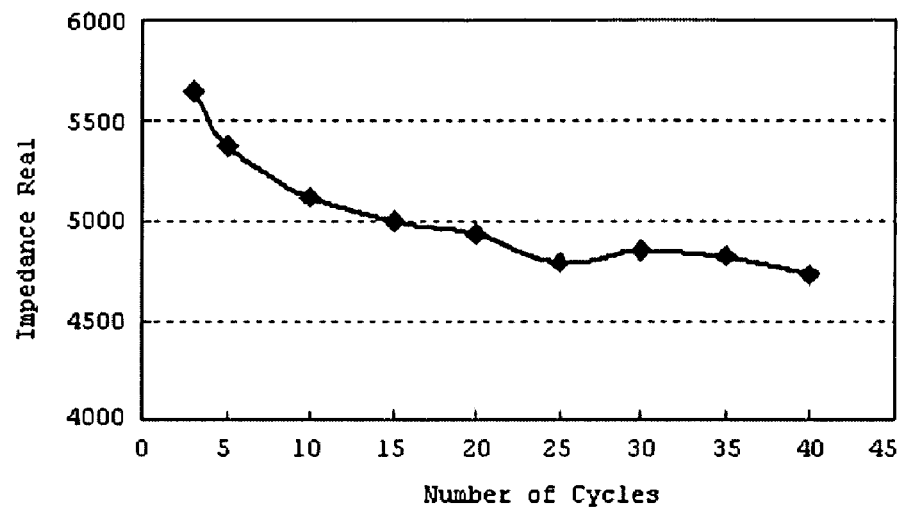
FIG. 5 illustrates the impedance values of an amplified product measured at 10,000 Hz with 10 mV of alternating current voltage and $10^6$ copies of HBV DNA during 40 cycles, with respect to the number of PCR cycles.
Figure 6:
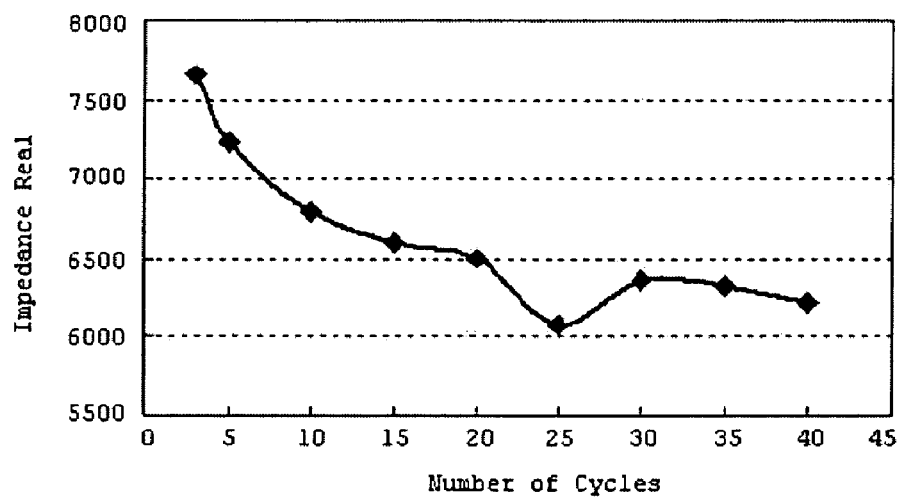
FIG. 6 illustrates the impedance values of an amplified product measured at 1,000 Hz with 10 mV of alternating current voltage and $10^6$ copies of HBV DNA during 40 cycles, with respect to the number of PCR cycle.

Results obtained through the above experiments are illustrated in FIGS. 2 through 6. FIG. 2 is a Bode plot illustrating the results measured for a 1,000-100,000 Hz sweep at 10 mV of an alternating current voltage and 10$^6$ copies of HBV DNA (template DNA) during 40 cycles. FIG. 3 is a Nyquist plot of the results of FIG. 2. FIGS. 4 through 6 illustrate impedance values of the amplified product measured at 100,000 Hz, 10,000 Hz, and 1,000 Hz, respectively, and with 10 mV of alternating current voltage and 10$^6$ copies of HBV DNA during 40 cycles, with respect to the number of PCR cycles.

Referring to FIGS. 4 through 6, as the PCR proceeded, the concentration of the amplified DNA increased and the resistance of the PCR mixture diminished due to the electrical function of the double helix structure.

Example 3: Coating of a Polyanionic Polymer and Measurement of an Electrical Signal of a Real-Time PCR The inner surface of an amplification chamber (material: glass, capacity 1 µl) included in a micro PCR chip was coated by adding 3 g/mL of PSS in 0.5M NaCl to the amplification chamber and leaving it for 20 minutes. Then, the coated inner surface was washed with distilled water and left for 30 minutes or more to dry.

The formation of a coating layer was identified by measuring the contact angle of the inner surface of the amplification chamber coated with the polyanionic polymer, using a contact angle meter (FACE, Japan). Then, as described in Example 2, a PCR was performed, and the concentration of the PCR product was measured in real time. The results of the measured contact angle are shown in Table 2.

TABLE 2

Contact angle of the amplification chamber with the polyanionic polymer layer (unit: degrees)

| Surface to be coated | Before coating | After coating |
| --- | --- | --- |
| Glass (SiO$_2$) surface | 45 ± 0.5 | 22 ± 0.5 |
| Platinum electrode | 91 ± 0.5 | 72 ± 0.5 |

Referring to Table 2, the contact angle decreased after coating the amplification chamber with the polyanionic polymer to a similar level as shown in Table 1, indicating that the coating layer was formed. Also, the impedance of the PCR product was measured in real time during the PCR. As a result, as the number of PCR cycles increased, the resistance of the PCR mixture decreased.

Example 4: Coating of a Polycationic Polymer and then a Polyanionic Polymer and Measurement of an Electrical Signal of a Real-Time PCR As described in Example 1, an amplification chamber was coated with a polycationic polymer of PDADMAC, and then, as described in Example 3, the amplification chamber was coated with a polyanionic polymer of PSS. Then, as described in Example 2, a PCR was performed and the concentration of the PCR product was electrically measured.

The results of the measured contact angle were similar to the results of Example 3, and the impedance value of the PCR mixture containing the PCR product reproducibly decreased as the PCR proceeded.

As described above, a polyanionic polymer or a polycationic polymer was coated on an inner surface of an amplification chamber so that the concentration of an amplified product can be measured using an electrical signal reproducibly. Also, the inner surface of the amplification chamber was coated with a material having an electric charge so that bubbles can be prevented from generating during microflowing a sample.

When using a micro PCR device according to an embodiment of the present invention, a PCR can be performed while reproducibly measuring the concentration of a PCR product, using an electrical signal.

When using a method of amplifying a nucleic acid according to another embodiment of the present invention, a nucleic acid can be amplified while reproducibly measuring the concentration of a PCR product, using an electrical signal.

When using a method of measuring the concentration of a PCR product according to another embodiment of the present invention, the concentration of the PCR product can be reproducibly measured using an electrical signal while performing a PCR.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A micro PCR device comprising
   an amplification chamber, the amplification chamber having an inner surface coated only with a polycationic polymer;
   at least a pair of electrodes including a first electrode attached to a first inner surface and a second electrode attached to a second inner surface, wherein the first inner surface and the second inner surface face each other and the electrodes face each other to generate an electric field between the electrodes; and
   a detector for detecting an electrical signal generated from a PCR solution, wherein the detector is electrically connected to the electrodes,
   wherein the first electrode and the second electrode are coated with the polycationic polymer.

2. The micro PCR device of claim 1, wherein the polycationic polymer is a polymer selected from the group consisting of polylysine, poly(diallyl dimethyl ammonium chloride) (PDADMAC), poly(allylamine hydrochloride) (PAH), and poly(ethylene imine) (PEI).

3. The micro PCR device of claim 1, wherein the inner surface is composed of a polycationic polymer which is coated on a polyanionic polymer layer.

4. The micro PCR device of claim 1, further comprising an impedance analyzer.

5. A method of amplifying a nucleic acid, the method comprising:
   adding a PCR mixture to an amplification chamber in the micro PCR device of claim 1 so as to allow the PCR mixture to adsorb to the amplification chamber; and
   performing a PCR.

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
gtggctttgg ggcatggaca tt                                          22

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
ctctaaggcc tcccgataca g                                           21

6. A method of detecting a PCR product, the method comprising:
adding a PCR mixture to an amplification chamber in the micro PCR device of claim 1 so as to allow the PCR mixture to adsorb to the amplification chamber;
performing a PCR;
generating an electric field between electrodes; and
measuring an electrical signal of the PCR mixture.

7. The method of claim 6, wherein the electrical signal is a signal for impedance, dielectric loss, dielectric constant, or admittance.

8. The method of claim 6, wherein in the generating of an electric field, an alternating current with a frequency range of 1 Hz -100 MHz is used.

9. The method of claim 6, wherein in the generating of an electric field, an alternating current voltage of 1 mV 10 V average voltage (Vrms) is used.

10. The micro PCR device of claim 1, wherein the electrical signal is a signal for impedance, dielectric loss, dielectric constant or admittance.

11. A method of amplifying a nucleic acid, the method comprising:
adding a PCR solution to an amplification chamber in the micro PCR device of claim 1 so as to allow the PCR solution to adsorb to the amplification chamber; and
performing a PCR.

12. A method of detecting a PCR product, the method comprising:
adding a PCR solution to an amplification chamber in the micro PCR device of claim 1 so as to allow the PCR solution to adsorb to the amplification chamber;
performing a PCR;
generating an electric field between electrodes during PCR; and
measuring an electrical signal of the PCR solution.

* * * * *